(12) United States Patent
Bhotla et al.

(10) Patent No.: US 7,915,430 B2
(45) Date of Patent: *Mar. 29, 2011

(54) CATALYTIC METHOD FOR PRODUCING PHENOLPHTHALEIN COMPOUNDS

(75) Inventors: Venkata Rama Narayanan Ganapathy Bhotla, Karnataka (IN); Shivappa Basappa Halligudi, Maharasthra State (IN); Gurram Kishan, Karnataka (IN); Salkod Parameshwar Mallika, Karnataka (IN); Bhaskar Veldurthy, Karnataka (IN)

(73) Assignee: Sabic Innovative Plastics IP B.V. (NL)

( * ) Notice: Subject to any disclaimer, the term of this patent is extended or adjusted under 35 U.S.C. 154(b) by 155 days.

This patent is subject to a terminal disclaimer.

(21) Appl. No.: 12/239,908

(22) Filed: Sep. 29, 2008

(65) Prior Publication Data

US 2010/0081828 A1  Apr. 1, 2010

(51) Int. Cl.
C07D 209/48 (2006.01)
C07D 307/20 (2006.01)
(52) U.S. Cl. ..................... 549/308; 548/485
(58) Field of Classification Search .......... 548/485; 549/308
See application file for complete search history.

(56) References Cited

U.S. PATENT DOCUMENTS

| | | | |
|---|---|---|---|
| 2,192,485 A | 3/1940 | Hubacher | |
| 2,522,939 A | 9/1950 | Gamrath | |
| 2,522,940 A | 9/1950 | Gamrath | |
| 4,252,725 A | 2/1981 | Prindle et al. | |
| 6,573,405 B1 | 6/2003 | Abbott et al. | |
| 7,041,774 B2 | 5/2006 | Kishan et al. | |
| 7,045,482 B2 | 5/2006 | Chun et al. | |
| 2008/0177091 A1 | 7/2008 | Basale et al. | |
| 2010/0081829 A1* | 4/2010 | Bhotla et al. ......... | 548/485 |

FOREIGN PATENT DOCUMENTS

WO 2008/091368 A1 7/2008

OTHER PUBLICATIONS

International Search Report for PCT/IB2009/054170, mailing date Nov. 16, 2009, 6 pages.
Written Opinion of International Search Report for PCT/IB2009/054170, mailing date Nov. 16, 2009, 7 pages.
Yin, et al., "High Regioselective Diels-Alder Reaction of Myrcene with Acrolein Catalyzed by Zinc-Containing Ionic Liquids," Adv. Synth. Catal., 347, (2005) pp. 137-142.
Bordoloi, et al., "Liquid-phase Veratrole Acylation and Toluenme Alkylation Over WOx/ZrO2 Solid Acid Catalysts," Journal of Molecular Catalysis A: Chemcial, 247, (2006) pp. 58-64.

International Search Report for PCT/IB2009/054075, mailing date Apr. 9, 2010, 6 pages.
Written Opinion of International Search Report for PCT/IB2009/054075, mailing date Apr. 9, 2010, 6 pages.

* cited by examiner

Primary Examiner — Yong Chu
(74) Attorney, Agent, or Firm — Cantor Colburn LLP

(57) ABSTRACT

A method of producing a phenolphthalein comprises reacting a phenolic compound of the formula:

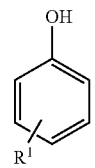

wherein $R^1$ is a hydrogen or a $C_1$-$C_{12}$ hydrocarbyl group, with a phthalic anhydride compound of the formula:

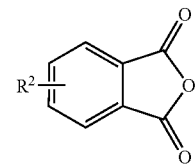

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

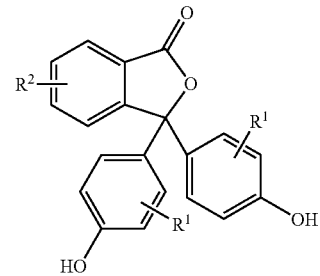

wherein each $R^1$ is independently a hydrogen or a $C_1$-$C_{12}$ hydrocarbyl group, and $R^2$ is a hydrogen, a $C_1$-$C_{12}$ hydrocarbyl group, or a halogen; wherein the heterogeneous catalyst comprises a metal oxide composition in combination with a porous support, wherein the metal is molybdenum, tungsten, or a combination comprising at least one of the foregoing metals.

20 Claims, No Drawings

CATALYTIC METHOD FOR PRODUCING PHENOLPHTHALEIN COMPOUNDS

BACKGROUND

This disclosure is directed to methods of manufacturing phenolphthalein compounds, in particular methods using a metal oxide catalyst.

Phenolphthalein compounds are useful as a starting material to make a wide range of products. For example, phenolphthalein compounds are important raw materials for the synthesis of 3,3-bis(4-hydroxyphenyl)phthalimidine and 2-hydrocarbyl-3,3-bis(4-hydroxyaryl)phthalimidines, in particular 2-phenyl-3,3-bis(4-hydroxyphenyl)phthalimidine (PPPBP). These phthalimidine compounds can be used in the manufacture of homopolycarbonates and copolycarbonates.

Phenolphthalein has been produced in a homogenous process in which phthalic anhydride is reacted with phenol in the presence of zinc chloride ($ZnCl_2$) as a catalyst. In U.S. Pat. No. 2,522,939, Gamrath disclosed improving this widely used process by the addition of chlorosulphonic acid as an activating agent (also referred to as a promoter) for the zinc chloride. This process has become commercially used because of the high purity, selectivity, and yield obtained.

Presently available manufacturing processes for phenolphthalein are time consuming and require large amounts of energy and chemicals, as well as complex equipment. U.S. patent application Ser. No. 11/626,671 discloses an improved method for producing and purifying phenolphthalein compounds on a commercial scale that requires fewer resources. In particular, after reacting a phthalic anhydride compound and a phenol compound in the presence of a catalyst and a promoter to form a reaction mixture comprising the phenolphthalein compound, the reaction mixture is treated with a solvent system to form a slurry. The slurry can then be filtered to obtain a solid material, which, after washing in water at an elevated temperature, comprises the phenolphthalein compounds in high purity. This commercial process, however, still employs zinc chloride and chlorosulphonic acid to catalyze the reaction.

There are several significant challenges associated with processes for manufacturing phenolphthalein using zinc chloride. In commercial practice, the zinc chloride is used in relatively large amounts, 0.6 mole of zinc chloride per mole of phthalic anhydride. The used catalyst must be separated from the reaction mixture after quenching of the reaction. The difficulty of separating the catalyst, which is used in slurry form, is increased because the slurry becomes very viscous over time. Importantly, the large amounts of used catalyst cannot be reused and must be disposed of safely.

It would be desirable to develop a process for the preparation of phenolphthalein compounds wherein the catalyst is more readily separated from the reaction mixture. It would further be desirable to develop a process for the preparation of phenolphthalein compounds that reduces waste generation, for example by allowing the catalyst to be reused. It would also be desirable if these processes provided phenolphthalein compounds of high purity.

BRIEF SUMMARY OF THE INVENTION

Some or all of the above-described deficiencies are addressed by a method for producing a phenolphthalein compound comprising: reacting a phenolic compound of the formula:

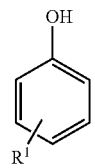

wherein $R^1$ is a hydrogen or a $C_1$-$C_{12}$ hydrocarbyl group, with a phthalic anhydride compound of the formula:

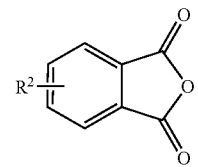

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

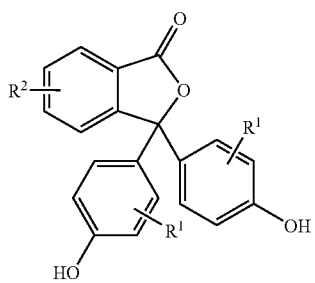

wherein each $R^1$ is independently a hydrogen or a $C_1$-$C_{12}$ hydrocarbyl group, and $R^2$ is a hydrogen, a $C_1$-$C_{12}$ hydrocarbyl group, or a halogen; wherein the heterogeneous catalyst comprises a metal oxide composition in combination with a porous support, wherein the metal is molybdenum, tungsten, or a combination comprising at least one of the foregoing metals.

In another embodiment, a method for producing a phenolphthalein comprises: reacting a phenolic compound of the formula:

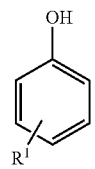

wherein $R^1$ is a hydrogen, with a phthalic anhydride compound of the formula:

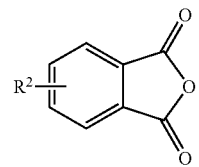

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

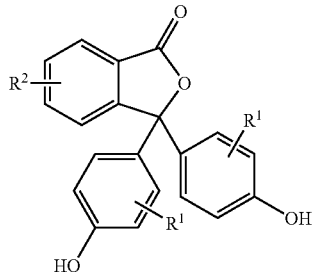

wherein each $R^1$ is a hydrogen, and $R^2$ is a hydrogen, a $C_1$-$C_{12}$ hydrocarbyl group, or a halogen; wherein the heterogeneous catalyst comprises an oxide of tungsten or an oxide of molybdenum in combination with a zirconium oxide support, a cerium oxide support, or a zirconium oxide-cerium oxide support; quenching the reaction mixture comprising the phenolphthalein compound to provide a first quenched reaction mixture; mixing the first quenched reaction mixture with a first organic solvent in which the phenolphthalein compound dissolves to provide a second quenched reaction mixture comprising dissolved phenolphthalein compound; filtering the second quenched reaction mixture to provide a solid residue comprising the heterogeneous catalyst and a filtrate comprising the organic solvent and the phenolphthalein compound; removing the organic solvent from the filtrate to provide a residue comprising the phenolphthalein compound; and regenerating the heterogeneous supported catalyst.

In still another embodiment, a method for producing a phenolphthalein compound comprises: reacting a phenolic compound of the formula:

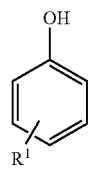

wherein $R^1$ is a hydrogen or a $C_1$-$C_{12}$ hydrocarbyl group, with a phthalic anhydride compound of the formula:

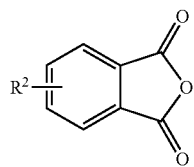

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

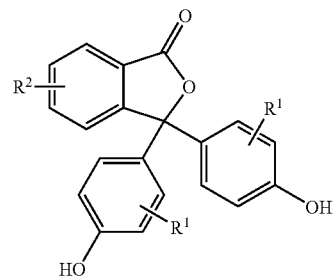

wherein each $R^1$ is independently a hydrogen or a $C_1$-$C_{12}$ hydrocarbyl group, and $R^2$ is a hydrogen, a $C_1$-$C_{12}$ hydrocarbyl group, or a halogen;
wherein the heterogeneous catalyst comprises a sulfated Group IVB metal oxide, a lanthanide series metal oxide, or a combination comprising at least one of the foregoing metal oxides.

The invention is further illustrated by the following detailed description and claims.

DETAILED DESCRIPTION

The inventors hereof have discovered that use of specific heterogeneous catalysts in a process for the manufacture of phenolphthalein allows ready separation of the catalyst from the reaction mixture, thereby providing a more efficient and less waste generating (eco-friendly) process. It has further been found that the catalyst can be regenerated and reused, which again provides a more efficient, less wasteful, and eco-friendly process. In a still further advantage, use of the heterogeneous, supported metal oxide catalyst provides phenolphthalein compounds of high purity.

In one embodiment, the heterogeneous catalyst comprises a metal oxide in combination with a porous support. The metal oxide comprises molybdenum, tungsten, or a combination comprising at least one of molybdenum and tungsten. The porous support is another metal oxide, for example zirconium oxide, cerium oxide, or other oxide such as silica.

In another embodiment, the heterogeneous catalyst comprises a sulfated metal oxide support, in particular a sulfated zirconium oxide.

The metals in the catalyst or in the support are not limited to any particular valence state. These metals can be present in the catalyst or support in any possible positive oxidation for the metal species. "Metal oxide" as used herein means compositions comprising the metal oxide, which may or may not further comprise the corresponding metal hydroxides and/or waters of hydration. Thus, a "metal oxide" refers qualitatively to compositions wherein an elemental analysis reveals the presence of the relevant metal (in one or more valence states) and oxygen. For example, an exemplary porous support disclosed herein is a zirconia having the formula $ZrO_2(OH)_x$. As is understood by those of skill in the art, the amount of oxygen measured in such an analysis will depend on a number of factors such as the valence state of the metal, for example a Group IVB or Group VIB metal, moisture content, and the like. For convenience, the metal oxides and porous supports can be referred to herein using formulas such as $XO_w/YO_z$ wherein, for example, X is a Group IVB metal such as zirconium, and Y is a Group VIB metal such as molybdenum or tungsten. It will be appreciated, however, that this notation is for convenience, and one or both the metal oxides as represented by $XO_w$ and $YO_z$ may comprise the corresponding hydroxides and/or contain waters of hydration. Thus, the heterogeneous catalysts described herein are not subject to a single specific formula for every embodiment.

Where the heterogeneous catalyst comprises a metal oxide in combination with a porous support, the metal oxide comprises molybdenum, tungsten, or a combination of metals comprising at least one of molybdenum and tungsten. Tungsten-containing oxide materials can be represented by $WO_x$, which includes $WO_3$ or $W_2O_6$. Molybdenum-containing oxide materials can be represented by $MoO_x$, which includes $MoO_3$ or $Mo_2O_6$. Other species, for example other metals can be present, provided that such species do not significantly adversely affect the use of the heterogeneous catalyst as described herein Where the heterogeneous catalyst comprises a metal oxide in combination with a porous support, various porous materials can be used as the support. Such materials included, for example, zirconium oxide (zirconia, $ZrO_2$), titanium oxide (titania, $TiO_2$ (anatase or rutile)), a lanthanide series metal oxide such as cerium oxide (ceria, $CeO_2$), aluminosilicates, silica ($SiO_2$), aluminum oxide (alumina, $Al_2O_3$ (acidic or neutral)), zinc oxide, magnesium oxide, niobium oxide, tin oxide, and combinations comprising at least one or more of the foregoing materials. Aluminosilicates, for example, can include various zeolites such as the SBA series of zeolites, such as SBA-11, SBA-12, and SBA-15. Other exemplary types of zeolites include mordenite, ZSM-5, L-zeolite, faujasite, ferrierite, and chabazite.

In one specific embodiment, the porous support is silica, cerium oxide, zirconium oxide, or cerium oxide-zirconium oxide. Tungsten oxide in combination with a zirconium oxide porous support is sometimes referred to as tungstated zirconia, $WO_x/ZrO_2$, and tungsten oxide in combination with a cerium oxide porous support is sometimes referred to as tungstated ceria, $WO_x/CeO_2$. In a specific embodiment, the heterogeneous catalyst is tungsten oxide in combination with zirconium oxide, tungsten oxide in combination with cerium oxide, tungsten oxide in combination with zirconium oxide-cerium oxide, or molybdenum oxide in combination with silicon oxide.

When the heterogeneous catalyst is a sulfated porous Group IVB metal oxide, a lanthanide series metal oxide, or a combination comprising at least one of the foregoing oxides, the metal oxide acts as a support. Catalysts of this type include sulfated zirconium oxide, sulfated cerium oxide, and combinations comprising at least one of the foregoing.

In either embodiment, the porous support can be a microporous or a mesoporous material. Mesoporous supports have a pore size of greater than or equal to about 10 to about 100 angstroms, and the microporous supports have a pore size of less than or equal to about 10 angstroms, as determined by BET measurements. The heterogeneous catalyst has a surface area of 10 to 600 m²/g, specifically 20 to 200 m²/g, measured in accordance with the BET method. The surface density of the tungsten or molybdenum (or both) in the heterogeneous catalyst is 2 to 30, specifically 3 to 12, atoms per amount nanometer square area, as determined according to the method of A Bordoloi et al, *Journal of Molecular Catalysis A; Chemical* 247 (2006) 58-64, page 60.

The heterogeneous catalysts can be made by a variety of methods. In one embodiment, the heterogeneous catalyst is manufactured by contacting (e.g., impregnating) a precursor of the porous support with a metal oxide precursor or sulfate anion precursor; and calcining the combined precursors. Other species, for example other metals, can be present during the reactions, provided that such species do not significantly adversely affect the use of the heterogeneous catalyst as described herein.

The precursor for the porous support comprises the metal oxide itself, a metal oxyhydroxide thereof, a metal hydroxide thereof, or a combination comprising at least one of the foregoing. One precursor of tungsten or molybdenum oxide is the corresponding oxyanions. Thus, in one embodiment, the heterogeneous catalyst comprises the reaction product of an oxyanion of molybdenum, an oxyanion of tungsten, or a combination of an oxyanion of molybdenum and oxyanion of tungsten with a porous support precursor. For example, ammonium metatungstate $(NH_4)_6H_2W_{12}O_{40} \cdot xH_2O$ (also known as AMT, wherein the molecular weight of the anhydrous portion, is 2956 Daltons) is commercially available in the form of highly soluble hydrated crystals, which can be used in powder form as a source of water-soluble tungsten. At room temperature, aqueous solutions can be saturated up to 70% by weight of contained $WO_3$. The porous support, such as a hydroxide of zirconium, is contacted with AMT, then water removed by drying and calcination, as described further in the examples below.

The amount of metal oxide or sulfate anions in the heterogeneous catalyst varies, depending on the type of metal oxide, the type of support, the desired activity of the heterogeneous catalyst, and like considerations. For example, the total amount of metal oxide is 5 to 30 weight percent (wt. %), specifically 10 to 20 wt. %, based on the weight of the support.

The heterogeneous catalysts are useful to catalyze the reaction of a phenolic compound and a phthalic anhydride compound to produce a phenolphthalein compound. The phenolic compound is of formula (I):

(I)

wherein $R^1$ is a hydrogen or $C_1$-$C_{12}$ hydrocarbyl group, specifically a hydrogen, $C_1$-$C_3$ alkyl, or $C_1$-$C_3$ alkoxy. In one embodiment, $R^1$ is a hydrogen.

The phthalic anhydride compound is of formula (II):

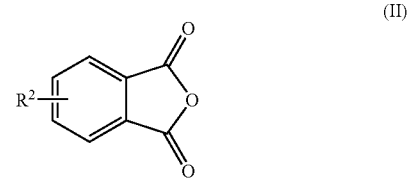

(II)

wherein $R^2$ is a hydrogen, a $C_1$-$C_{12}$ hydrocarbyl group, or a halogen, specifically a hydrogen, $C_1$-$C_3$ alkyl, $C_1$-$C_3$ alkoxy, bromine, or chlorine. In one embodiment, $R^2$ is a hydrogen.

The phenolphthalein compound produced in the reaction is of formula (III):

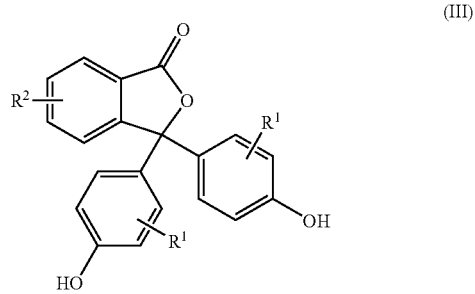

(III)

wherein each $R^1$ is independently a hydrogen or a $C_1$-$C_{12}$ hydrocarbyl group; and $R^2$ is a hydrogen, a $C_1$-$C_{12}$ hydrocarbyl group, or a halogen. In a specific embodiment, each $R^1$ is the same, and is a hydrogen, $C_1$-$C_3$ alkyl, or $C_1$-$C_3$ alkoxy; and $R^2$ is $C_1$-$C_3$ alkyl, $C_1$-$C_3$ alkoxy, bromine, or chlorine. In another embodiment, each $R^1$ is a hydrogen, and $R^2$ is a hydrogen.

The phenolic compound is reacted with the phthalic anhydride compound in the presence of the heterogeneous catalyst and a co-catalytically effective amount of a promoter. Exemplary promoters include chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, and combinations comprising at least one of the foregoing promoters. Specific promoters include chlorosulphonic acid, methanesulphonic acid, dodecylbenzenesulphonic acid, triflic acid, boron trifluoride, p-toluene sulphonyl chloride, and combinations comprising at least one of the foregoing. In one embodiment, the promoter is chlorosulphonic acid.

The reaction is typically carried out using a stoichiometric excess of the phenolic compound relative to the phthalic anhydride. In one embodiment, the reaction is carried out using a molar ratio of the phthalic anhydride compound to the phenolic compound of 1:2.1 to 1:10, specifically 1:2.1 to 1:3, more specifically 1:2.1 to 1:2.5.

The amount of the heterogeneous catalyst used in the reaction varies, depending on the type of heterogeneous catalyst, its activity, the desired time for the reaction, and like considerations. In general, the amount of heterogeneous catalyst is 10 to 30 wt. %, specifically 12 to 25 wt. %, more specifically 15 to 20 wt. %, based on the weight of phenolic compound and the phthalic anhydride compound.

The promoter is present in an amount of up to 6 mol %, more specifically, 0.05 to 5 mol %, based on the moles of phthalic anhydride. Specifically, chlorosulphonic acid is present in an amount of 0.05 to 0.5 molar equivalents, more specifically 0.1 to 0.3 molar equivalents, with respect to the phthalic anhydride compound.

The conditions for the reaction vary, depending on the particular phenolic compound, phthalic anhydride compound, heterogeneous catalyst, and promoter. In one embodiment, the reaction is conducted at elevated temperature, for example, a temperature of 90° C. to 175° C., specifically 100 to 175° C., more specifically 110 to 165° C., for a reaction time of 10 to 100 hours, specifically 20 to 70 hours, more specifically 30 to 60 hours. The progress of the reaction can be followed by numerous analytical techniques such as gas chromatography or high-pressure liquid chromatography (HPLC).

Following reaction, the reaction mixture comprising the product phenolphthalein compound is typically quenched. Quenching is done, for example, by the addition of a protic organic solvent such as methanol.

The phenolphthalein compound is isolated from the reaction mixture or quenched reaction mixture. In one embodiment, the phenolphthalein compound is isolated by the addition of a solvent in which the phenolphthalein compound is soluble, in an amount effective to dissolve the phenolphthalein compound. The heterogeneous catalyst is separated from this mixture, for example by filtering or centrifugation. The filtrate or supernatant is then treated to remove the solvent, for example by distilling the methanol to provide a residue comprising the phenolphthalein compound.

The residue is then heated with a less polar solvent, for example toluene, to precipitate the crude phenolphthalein compound. The crude phenolphthalein product is then isolated by, for example, filtration, and washing with a water or other solvent. The phenolphthalein compound after this step is obtained at a purity of 80 wt. % or greater, specifically 90 to 99 wt. %, more specifically 94 to 97 wt. %, based on the total weight of crude phenolphthalein product (reaction product obtained after removal of the heterogeneous catalyst, precipitation with a less polar solvent, and washing of the reaction product with water or other solvent). The phenolphthalein compound is obtained in a molar yield of greater than or equal to 70%, specifically greater than 80% yield, based on the moles of phthalic anhydride compound. In one embodiment, the phenolphthalein compound is obtained both at a purity of greater than 80 wt. %, specifically 90 to 99 wt. %, more specifically 94 to 97 wt. %, based on the total weight of crude phenolphthalein product, and in a molar yield of greater than or equal to 70%, specifically greater than 80% yield, based on the moles of phthalic anhydride compound.

In a particularly advantageous embodiment, the heterogeneous catalyst is regenerated after the reaction, and reused. Specifically, the heterogeneous catalyst is separated from the reaction mixture comprising the phenolphthalein compound, regenerated, and reused for at least one more cycle, for a total of 2 to 4 cycles, specifically 2 or 3 cycles, wherein the first use of the fresh catalyst is considered a first cycle. Without being bound by theory, it is believed that the regeneration removes organic reaction residues that adhere to the catalyst and adversely affect its activity.

In one embodiment, the heterogeneous catalyst is regenerated by calcination at elevated temperature, for example 400 to 900° C., specifically 450 to 750° C., more specifically at 450 to 550° C. for about 8 hours. Calcination is carried out in an inert atmosphere.

In another embodiment, regeneration of the heterogeneous catalyst comprises washing the used catalyst with a heated solvent at an elevated temperature, specifically at a temperature of 30 to 60° C. The heated solvent is a non-aqueous polar organic solvent, for example, methanol, phenol, ethyl acetate, acetone, chloroform, isopropanol, and combinations comprising at least one of the foregoing solvents. The solvent is removed by distillation or drying before reuse of the catalyst. In a specific embodiment, regeneration of the heterogeneous catalyst comprises washing the used, isolated heterogeneous catalyst with a non-aqueous polar organic solvent to remove adhered organics on the catalyst, then suspending the catalyst in the same or different non-aqueous polar solvent while heating to a temperature of 30 to 60° C. with stirring for 15 to 30 minutes. The catalyst is then isolated by filtration and dried in an oven, for example, for 2 to 4 hours at 30 to 100° C., and reused.

All or part of foregoing process can be conducted as a batch or continuous process. The ease of separating the catalyst and its regeneration can allow for a continuous process.

In a batch process, the reactants are stirred in the presence of the supported metal oxide catalyst. In a continuous process, the reactants are continuously introduced into at least one reactor comprising a fixed bed or fluidized bed packing comprising the supported catalyst at an appropriate temperature. For example, a continuous process is carried out in a single reactor packed with the supported catalyst, wherein the phenolic compound is passed continuously into the reactor and the phthalic anhydride compound is selectively introduced in one or more stages of the reactor. In other embodiments of a continuous process, a single or multiple reactor system comprising fixed bed packing of the supported catalyst further comprises packing structures designed to alleviate the hydraulic stress that generally results from prolonged operation. Such packing structures assume a variety of structures specially designed to withstand hydraulic stress and comprise materials inert to the reactive materials.

The heterogeneous catalysts and methods described herein provide several significant advantages. The heterogeneous catalysts provide excellent selectivity and yield, comparable to that obtained by the use of a catalyst system comprising zinc chloride. The heterogeneous catalyst is environmentally superior to the use of zinc chloride, since it reduces the effluent disposal problem. After completion of the reaction, the catalyst is readily separated from the reaction mixture, for example by simple filtration. The catalyst is regenerated and reused for at least one more reaction cycle. The original unused ("native") activity can be readily obtained, for example, by washing with solvent or calcination. The catalyst system enables operation in a continuous mode on an industrial scale.

The phenolphthalein compound is used as a starting material to make a wide range of products. For example, the phenolphthalein compound wherein each $R^1$ and $R^2$ are hydrogen is converted to PPPBP by known methods, and then used as a monomer used in the manufacture of homopolycarbonates and copolycarbonates. Such polycarbonates exhibit high transparency, high glass transition temperatures, and other advantageous properties.

The above-described processes are further illustrated by the following non-limiting examples.

EXAMPLES

Preparation of Tungsten Oxide on Zirconia.

A catalyst containing 15% by weight, based on weight of catalyst and support, of tungsten oxide on a zirconia support ($WO_3/ZrO_2$) was prepared by wet impregnation using ammonium metatungstate as a tungsten precursor and zirconium oxyhydroxide ($ZrO(OH)_x$) as the material for making the support.

Zirconium oxyhydroxide was prepared by dissolving 50 g of $ZrOCl_2.8H_2O$ in 1 L of distilled water. To this solution, aqueous ammonia was added slowly with stirring to precipitate zirconium oxyhydroxide. Ammonia was added slightly in excess (until the smell of ammonia persisted) to ensure complete precipitation. The precipitate obtained was filtered, washed a number of times until free from chloride (as measured by testing the filtrate with $AgNO_3$), dried at 120° C. for 12 hours, powdered, and then dried for another 12 hours. Approximately 20 g of the zirconium oxyhydroxide was obtained.

Subsequently, 3.18 g of ammonium metatungstate was added to 100 mL of distilled water. This solution was stirred for 30 min. Then, 20 g of the previously prepared zirconium oxyhydroxide was added to the solution and stirred for 24 hours. Excess water was then evaporated in a rotary evaporator. The mixture was dried in an oven at 120° C. for 12 hours, well powdered, again dried for 12 hours, and calcined with heating at a rate of 5° C./min to 730° C. for 4 hours. The supported catalyst was then cooled at the same rate to room temperature. Approximately 20 g of the 15 wt. % $WO_3/ZrO_2$ was obtained.

Preparation of Molybdenum Oxide on Silica.

A catalyst containing 20% by weight, based on weight of the catalyst and support, of molybdenum oxide on silica ($MoO_3/SiO_2$) was prepared by wet impregnation using tetraethyl orthosilicate as the precursor for the silica support and ammonium molybdate as the molybdenum oxide precursor.

In a typical synthesis, 20% $MoO_3/SiO_2$ was prepared by dissolving 12.3 g ammonium molybdate in 100 mL distilled water at 80° C. This hot solution was added dropwise to an isopropyl alcohol solution (100 mL) of tetraethyl orthosilicate (173.4 g) with constant stirring. The resultant greenish gel was aged for 48 hours, air dried and calcined at 500° C. in a furnace for 8 hours, yielding 15 g of 20 wt. % $MoO_3/SiO_2$.

Preparation of Tungsten Oxide on Ceria.

A catalyst containing 15% by weight, based on weight of the catalyst support, of tungsten oxide on a ceria support ($WO_3/CeO_2$) was prepared by wet impregnation using cerium nitrate ($Ce(NO_3).6H_2O$) as the support precursor and ammonium metatungstate as the tungsten precursor.

$Ce(OH)_x$ was prepared by dissolving 38 g of $Ce(NO_3).6H_2O$ in 350 mL of distilled water. To this solution aqueous ammonia was added slowly with stirring to precipitate $Ce(OH)_x$. Ammonia was added slightly in excess, until the smell of ammonia persisted, to ensure complete precipitation. The precipitate obtained was filtered and washed until the pH of the filtrate was 7, and then dried at 120° C. for 12 hours, powdered, and dried for another 12 hours. Approximately 15 g of the final product was obtained.

Subsequently, 2.3 g of ammonium metatungstate was added to 150 mL of distilled water. This solution was stirred for 30 minutes. Then, 15 g of the previously prepared $Ce(OH)_x$ was added into the solution and stirred for 24 hours. Excess water was then evaporated in a rotary evaporator, and the mixture was dried in an oven at 120° C. for 12 hours, well powdered, and again dried for 12 hours. The product was calcined with heating at a rate of 5° C./min to 730° C. for 4 hours and then cooled at the same rate to room temperature. Approximately 15 g of 15 wt. % $WO_3/CeO_2$ was obtained.

Preparation of Tungsten Oxide on Zirconia-Ceria.

A catalyst containing 15% by weight, based on weight of the catalyst support, of tungsten oxide on a zirconia-ceria support ($WO_3/ZrO_2$—$CeO_2$, in particular 15% $WO_3/CeZrO_2$ (90% $ZrO_2$+10% $CeO_2$)) was prepared by wet impregnation using cerium hydroxide and zirconium oxyhydroxide as the support precursors and ammonium metatungstate as the tungsten precursor.

The cerium and zirconium precursor was prepared by co-precipitation as follows. A first solution was prepared by dissolving 3.82 g of $Ce(NO_3).6H_2O$ in 22 mL of distilled water to obtain a 0.4 M solution. A second solution was prepared by dissolving 25.3 g of $ZrO(NO_3)_2$ in 273 mL of distilled water to obtain a 0.4 M solution of zirconyl nitrate. These first and second solutions were mixed thoroughly, and to this mixture aqueous ammonia was added slowly with stirring to precipitate the hydroxide of cerium-zirconium. Ammonia was added slightly in excess until the pH of the precipitate was about 10. The precipitate obtained was filtered and washed until the pH of the filtrate was 7, and then dried at 120° C. for 12 hours, powdered, and dried for another 12 hours. Approximately 15 g of the final product was obtained.

Subsequently, 2.39 g of ammonium metatungstate was added to 150 mL of distilled water. This solution was stirred for 15 minutes. Then, 14.56 g of the previously prepared precipitated support precursor was added into the solution and stirred for 12 hours. Excess water was then evaporated in a rotary evaporator, and the mixture was dried in an oven at 110° C. for 6 hours, well powdered, and again dried for at 110° C. for 12 hours. The product was calcined with heating at a rate of 5° C./min to 730° C. for 4 hours and then cooled at the same rate to room temperature. Approximately 15 g of 15 wt. % $WO_3/(90\% ZrO_2+10\% CeO_2)$ was obtained.

Preparation of Sulfated Zirconia Catalyst.

A sulfated zirconia catalyst was prepared by wet impregnation using zirconium oxyhydroxide as the support precursor and ammonium persulfate as the sulfate precursor.

First, zirconium oxyhydroxide was prepared by dissolving 40 g of $ZrOCl_2.8H_2O$ in 640 mL of distilled water. To this solution aqueous ammonia was added slowly with stirring to precipitate zirconium oxyhydroxide. Ammonia was added slightly in excess, until the smell of ammonia persisted, to ensure complete precipitation. The precipitate obtained was filtered and washed a number of times until free from chloride (the filtrate was tested with $AgNO_3$), dried at 120° C. for 12 hours, powdered, and dried for another 12 hours. Approximately 15 g of the zirconium oxyhydroxide product was obtained.

Subsequently, 57.05 g of ammonium persulfate was dissolved in 250 mL of distilled water (1M solution of ammonium persulfate). This solution was stirred for 30 minutes. Then, 15 g of the previously prepared zirconium oxyhydroxide was added into the solution and stirred for 24 hours. The solution was filtered and the filtered material was dried in an oven at 120° C. for 12 hours, well powdered, and calcined with heating at a rate of 5° C./min to 600° C. for 4 hours and then cooled at the same rate to room temperature. Approximately 15 g of the resulting product, a sulfated zirconia, was obtained.

Methods of Analysis.

In order to measure the progress of the reaction, HPLC analysis was generally carried out by using a solution of about 25 milligrams of a sample from the reaction mixtures in the following examples dissolved in about 50 milliliters of acetonitrile:0.05% aqueous $H_3PO_4$ (70:30, v:v). The HPLC instrument was equipped with a C-8 (reverse phase) column maintained at a temperature of 40° C. and an ultraviolet detector capable of detecting components at a wavelength of 225 nanometers. A solvent mixture of acetonitrile and water with 0.02% $H_3PO_4$ of gradient elution was used. A flow rate was maintained at 1 mL per minute. Area percent purity was computed from the area value for each peak detected in the chromatogram divided by the total area from all peaks detected. To measure weight percent assay, calibration curves for phenol, phthalic anhydride, and phenolphthalein were first generated. Then the weight percent of a given component in a sample was calculated using these calibration curves.

The weight percent assay of isolated solid phenolphthalein was computed by calculating the phenol, phthalic anhydride content using suitable calibration graphs, and all other impurities were calculated using the response factor of phenolphthalein. The purity of phenolphthalein was calculated by subtracting the amount of phenol, phthalic anhydride, and "others" from 100.

Example 1

Preparation of Phenolphthalein: A Procedure for the Preparation of phenolphthalein using metal oxide catalysts is as follows. In a 250 mL, round bottom flask equipped with mechanical stirrer, thermometer, nitrogen inlet, and reflux condenser, 18.5 g of phthalic anhydride and 27.6 g of phenol were charged, followed by 10.0 g of heterogeneous catalyst (tungstated zirconia) and 1.9 g of chlorosulphonic acid ("CSA"), while maintaining the round bottom flask in a nitrogen atmosphere at 50 to 60° C. This amounted to 2.25 molar equivalents of phenol with respect to the phthalic anhydride, and 17% by weight loading of the catalyst.

The reaction mixture was then heated with stirring at 140° C. (bath temperature). During the course of the reaction for 48 hours, the reaction mass progressively turned from orange to brownish orange to deep brown. The reaction product was then quenched (stopped) with a solvent (160 mL of methanol). The quenched mass comprising phenolphthalein (PP), unreacted phthalic anhydride (PA), and by-products was stirred at 85° C. for about 30 minutes. All organic compounds including the phenolphthalein dissolved in the methanol. The solution was then filtered to remove the solid catalyst as a residue and obtain a filtrate. The methanol was removed from the filtrate using a Rotovac® evaporator, and the viscous mass was then heated with 160 mL of toluene solvent and stirred at 85° C. for 30 minutes. The toluene removed unreacted reactants and by-products. The solid, crude precipitate, which did not dissolve in the toluene, was filtered while hot and washed with hot water. The resulting brownish yellow solid was dried under vacuum at 100° C. overnight to obtain crude phenolphthalein. The isolated yield of crude phenolphthalein was 35.0 g (88 wt. %, based on the phthalic anhydride), and the purity was 95.9%, as determined by HPLC as described above.

Phenolphthalein was prepared under the same conditions, except for using tungstated ceria and molybdenum on silica. The results of the various methods of preparing phenolphthalein are shown in Table 1 below, using the same analytical procedures as in Example 1. In Table 1, the "conversion" and "reaction yield" were determined just before quenching with methanol as described above. The "isolated yield" and "purity" in Table 1 refers to the crude phenolphthalein (after filtering and washing) according to the method described above.

TABLE 1

| No. | Catalyst Composition | Reaction Time/ Temperature | Conversion (wt. % PA) | Reaction Yield (wt. %) | Isolated Yield (wt. % PA) | Purity (wt. %) |
|---|---|---|---|---|---|---|
| 1 | 15 wt. % $WO_x/ZrO_2$ | 140° C. 48 hours | 98.8 | 85.1 | 88 | 95.9 |
| 2 | 15% wt. % $WO_x/ZrO_2$ | 165° C. 30 hours | 93.5 | 65.5 | 65 | 92 |
| 3 | 15 wt. % $(Mo)_x/SiO_2$ | 140° C. 48 hours | 92.0 | 51.5 | 50.0 | 89.0 |
| 4 | 20 wt. % $WO_x/ZrO_2$ | 140° C. 48 hours | 87.8 | 61.8 | 54 | 92 |
| 5 | 15 wt. % $WO_x/CeO_2$ | 140° C. 48 hours | 59.8 | 10.7 | NA | NA |
| 6 | 15 wt. % $WO_x/ZrO_2—CeO_2$ | 140° C. 48 hours | 99.3 | 80.5 | 84 | 95.6 |

TABLE 1-continued

| No. | Catalyst Composition | Reaction Time/ Temperature | Conversion (wt. % PA) | Reaction Yield (wt. %) | Isolated Yield (wt. % PA) | Purity (wt. %) |
|---|---|---|---|---|---|---|
| 7 | 15% $WO_x/ZrO_2$—$CeO_2$ with 0.3 mole eq. CSA | 140° C. 48 hours | 99.3 | 80.5 | 82 | 96.6 |
| 8 | Sulfated zirconia | 140° C. 48 hours | 93.3 | 69 | 73 | 96.3 |

PA (phthalic anhydride),
CSA (chlorosulphonic acid),
NA (data not available)

The results in Table 1 for Samples 1 to 8 showed that high purity phenolphthalein product was obtained in good yield using the heterogeneous catalysts and methods as described herein. When ceria was used as a support, a lower surface area resulted in relatively less yield. In all other cases, the exemplary supported catalysts provided a purity of greater than 90 weight percent. For these cases, the yield of isolated product varied from 50 to 88 weight percent. The temperature was shown to affect the results to some extent, so that temperature optimization can be used.

Example 2

To demonstrate regeneration of the supported catalyst, phenolphthalein was prepared using 1 molar equivalent of phthalic anhydride to 2.25 molar equivalent of phenol with respect to the phthalic anhydride in the presence of 15% tungstated zirconia. The temperature of the reaction was 165° C. and the reaction time was 30 hours.

The product was isolated by quenching the reaction with methanol, filtering the catalyst, and distilling the methanol as described above. The residue was heated with toluene at 85° C. to obtain a solid that was filtered, washed with hot water, and dried. The used catalyst was obtained as a residue from the filtering operation.

In one example, the catalyst was regenerated by calcination at 500° C. The catalyst was then reused to make phenolphthalein.

In another example, the catalyst was again used to make phenolphthalein, but this time the catalyst was regenerated by washing with methanol in a first recycle. The catalyst was reused a second time, again after isolation and regeneration by washing with methanol.

Finally, in yet another example, fresh tungstated zirconia was again used to prepare phenolphthalein, but this time the reaction temperature was 140° C. and the reaction time was 48 hours. HPLC was used to track the progress of the reaction, as described above under methods of analysis.

The reactions and results are summarized in Table 2. In Table 2, the "conversion" and "reaction yield" were determined after reaction and before quenching with methanol as described above. The "isolated yield" and "purity" in Table 2 refer to crude phenolphthalein (after filtering and washing) as described above.

TABLE 2

| No. | Catalyst Composition | Cycle | Method of Regeneration | Reaction Temp./ Time | Conversion (wt. % PA) | Reaction Yield (wt. %) | Isolated Yield (wt. % PA) | Purity (wt. %) |
|---|---|---|---|---|---|---|---|---|
| 1 | 15 wt. % $WO_x/ZrO_2$ | Fresh | None | 140° C. 48 hours | 98.8 | 85.1 | 88 | 95.9 |
| 2 | 15 wt. % $WO_x/ZrO_2$ | Recycled once | Washed with methanol, dried at 120° C. for 8 hours | 140° C. 48 hours | 85.3 | 73.1 | 75 | 94.3 |
| 3 | 15 wt. % $WO_x/ZrO_2$ | Recycled once | Calcined at 500° C. for 8 hours | 140° C. 48 hours | 96.7 | 83.7 | 88 | 91.8 |
| 4 | 15 wt. % $WO_x/ZrO_2$ | Fresh | None | 165° C. 30 hours | 93.5 | 65.5 | 65 | 92 |
| 5 | 15 wt. % $WO_x/ZrO_2$ | Recycled once | Washed with methanol, dried at 120° C. for 8 hours | 165° C. 30 hour | 93.8 | 59.9 | 60 | 80.5 |
| 6 | 15 wt. % $WO_x/ZrO_2$ | Recycled second time | Washed with methanol, dried at 120° C. for 8 hours | 165° C. 30 hours | NA* | NA | 58 | 80.6 |
| 7 | 15 wt. % $WO_x/ZrO_2$ | Recycled third time | Recycled catalyst of Ex. 6. Calcined at 500° C. for 8 hours | 165° C. 30 hours | NA | NA | 64 | 91.1 |

PA—Phthalic Anhydride;
NA—data not available

The above data shows that the catalyst regenerated by methanol wash resulted in less yield and lower purity of phenolphthalein when compared to that of unused catalyst. However, the catalyst regenerated by calcination (Samples 3 and 7 Table 2), resulted in the same catalyst activity as unused catalyst, and the yield and the purity of phenolphthalein are comparable with that of unused catalyst.

Example 3

Phenolphthalein was prepared with tungstated zirconia with and without chlorosulphonic acid (CSA). As in Example 2, phenolphthalein was prepared with 1 molar equivalent of phthalic anhydride to 2.25 molar equivalent of phenol with respect to the phthalic anhydride. The temperature of the reaction was 165° C. and the reaction time was 30 hours.

The results for the reaction without CSA are shown in Table 3, and are based on the HPLC measurements as described under method of analysis above. The measurements were taken directly from the reaction mixture, without workup.

TABLE 3

| Time (hours) | Phthalic Anhydride (wt. %) | Phenol (wt. %) | Reaction Yield (wt. %) |
|---|---|---|---|
| 18 | 38.75 | 33.85 | 18.96 |
| 23 | 39.50 | 30.80 | 20.87 |
| 27 | 40.61 | 31.03 | 20.93 |
| 42 | 34.63 | 29.09 | 25.04 |
| 45 | 34.16 | 29.37 | 24.63 |
| 48 | 34.41 | 29.37 | 25.41 |

The percent conversion, based on unreacted phthalic anhydride, was calculated at 65.6%. It was impractical to isolate the phenolphthalein due to the low conversion. These results show that use of chlorosulphonic acid as co-catalyst for the reaction results in better conversion and yield.

In comparison, for phenolphthalein prepared with chlorosulphonic acid in an amount of 0.2 moles based on phthalic anhydride, the results are as shown in Table 4 below.

TABLE 4

| Time (hours) | Phthalic Anhydride (wt. %) | Phenol (wt. %) | Reaction Yield (wt. %) |
|---|---|---|---|
| 4 | 28.20 | 21.33 | 30.97 |
| 7 | 23.72 | 17.80 | 38.38 |
| 9 | 22.78 | 16.12 | 41.36 |
| 24 | 10.51 | 7.46 | 63.65 |
| 27 | 10.34 | 7.08 | 64.59 |
| 30 | 9.20 | 6.38 | 65.10 |
| 33 | 8.22 | 6.05 | 66.22 |
| 48 | 1.25 | 2.45 | 85.10 |
| Isolated (crude) PP | 0.44 | 0.14 | 95.83 (purity of isolated PP) |

PP—Phenolphthalein

As indicated by the results in Table 4 above, using tungstated zirconia catalyst for making phenolphthalein in the presence of the CSA promoter, the purity of the isolated phenolphthalein was 95.83% as in Table 4. It was also determined that the conversion was 98.75%.

The singular forms "a," "an," and "the" include plural referents unless the context clearly dictates otherwise. Unless defined otherwise, technical and scientific terms used herein have the same meaning as is commonly understood by one of skill in the art to which this invention belongs. The endpoints of all ranges directed to the same component or property are inclusive and independently combinable (e.g., ranges of "less than or equal to about 25 wt %, or, more specifically, about 5 wt % to about 20 wt %," is inclusive of the endpoints and all intermediate values of the ranges of "about 5 wt % to about 25 wt %," etc.).

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

As used herein, the term "hydrocarbyl" is defined as a monovalent moiety formed by removing a hydrogen atom from a hydrocarbon. Representative hydrocarbyls are alkyl groups having 1 to 12 carbon atoms, such as methyl, ethyl, propyl, butyl, pentyl, hexyl, heptyl, octyl, nonyl, undecyl, decyl, dodecyl, and the isomeric forms thereof; aryl groups having 6 to 12 carbon atoms, such as ring-substituted and ring-unsubstituted forms of phenyl, tolyl, xylyl, naphthyl, biphenyl, and the like; aralkyl groups having 7 to 12 carbon atoms, such as ring-substituted and ring-unsubstituted forms of benzyl, phenethyl, phenpropyl, phenbutyl, and the like; and cycloalkyl groups, such as cyclopropyl, cyclobutyl, cyclopentyl, cyclohexyl, cycloheptyl, cyclooctyl, and the like, as well as the corresponding oxides of the foregoing groups. The term "aryl" as used herein refers to an aromatic monovalent group containing only carbon in the aromatic ring or rings.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While various embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A method for producing a phenolphthalein compound comprising:

reacting a phenolic compound of the formula:

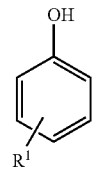

wherein $R^1$ is a hydrogen or a $C_1$-$C_{12}$ hydrocarbyl group, with a phthalic anhydride compound of the formula:

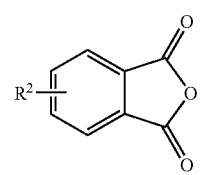

wherein $R^2$ is a hydrogen, a $C_1$-$C_{12}$ hydrocarbyl group, or a halogen, in the presence of a heterogeneous catalyst and a promoter to form a reaction mixture comprising a phenolphthalein compound of the formula:

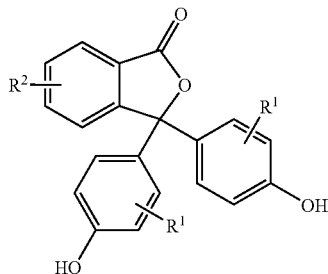

wherein each $R^1$ is independently a hydrogen or a $C_1$-$C_{12}$ hydrocarbyl group, and $R^2$ is a hydrogen, a $C_1$-$C_{12}$ hydrocarbyl group, or a halogen;
    wherein the heterogeneous catalyst comprises a metal oxide composition in combination with a porous support, wherein the metal is molybdenum, tungsten, or a combination comprising at least one of molybdenum and tungsten, and wherein the promoter is chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, or a combination comprising at least one of the foregoing promoters.

2. The method of claim 1, wherein the metal oxide is tungsten oxide or molybdenum oxide.

3. The method of claim 1, wherein the porous support is zirconium oxide, titanium oxide, cerium oxide, silicon oxide, aluminum oxide, magnesium oxide, niobium oxide, tin oxide, aluminosilicate, or a combination comprising at least one of the foregoing porous supports.

4. The method of claim 1, wherein the heterogeneous catalyst is tungsten oxide in combination with zirconium oxide, tungsten oxide in combination with cerium oxide, tungsten oxide in combination with zirconium oxide-cerium oxide, or molybdenum oxide in combination with silicon oxide.

5. The method of claim 1 wherein the heterogeneous catalyst comprises a metal oxide or mixed metal oxide catalyst in an amount of 5 to 30 wt.% based on the weight of the porous support.

6. The method of claim 1 wherein the heterogeneous catalyst is a tungsten oxide in an amount of 10 to 20 wt.%, based on the weight of the porous support.

7. The method of claim 1 wherein the amount of heterogeneous and combined with the porous support 10 to 30 wt.%, based on the weight of reactants.

8. The method of claim 1 wherein the promoter is chlorosulphonic acid.

9. The method of claim 1, wherein the phenolic compound is phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6-xylenol, 2,6-dichlorophenol, 3,5-diethylphenol, 2-benzylphenol, 2,6-di-tert-butylphenol, 2-phenylphenol, 1-naphthol, 2-naphthol, or a combination comprising at least one of the foregoing phenolic compounds.

10. The method of claim 1 wherein the stoichiometric molar ratio of the phthalic anhydride compound to the phenolic compound is 1:2.1 to 1:10.

11. The method of claim 1 wherein -reaction is conducted at a temperature of 90° C. to 175° C. for a reaction time of 10 to 100 hours.

12. The method of claim 1 wherein after reacting, the heterogeneous catalyst is separated from the reaction mixture, and then regenerated.

13. The method of claim 1 wherein the heterogeneous catalyst is used in a total of two to four cycles of reaction in a batch process.

14. The method of claim 1, wherein the heterogeneous supported catalyst is regenerated by calcination at a temperature of 400 to 900° C.

15. The method of claim 1, wherein the heterogeneous supported catalyst is regenerated by contacting with a non-aqueous polar organic solvent at a temperature of 30 to 60° C.

16. The method of claim 1, wherein the method further comprises:
    quenching the reaction mixture comprising the phenolphthalein compound with a first organic solvent in which the phenolphthalein compound dissolves to provide a first quenched reaction mixture;
    filtering the first quenched reaction mixture to provide a solid residue comprising the heterogeneous catalyst and a filtrate comprising the organic solvent and the phenolphthalein compound.

17. The method of claim 16, further comprising regenerating the heterogeneous catalyst in the solid residue.

18. The method of claim 16, further comprising
    removing the first organic solvent from the filtrate to provide a residue comprising the phenolphthalein compound;
    and heating the residue with a second, non-polar organic solvent to provide a precipitate comprising the phenolphthalein compound, wherein the phenolphthalein compound in the precipitate has a purity of greater than or equal to 80 weight percent, based on the weight of the precipitate, and the phenolphthalein compound is obtained in a yield of greater than or equal to 70 mole percent, based on the moles of the phthalic anhydride compound.

19. A method for producing a phthalimidine comprising producing a phenolphthalein compound according to the method of claim 1, and converting the phenolphthalein compound to the corresponding phthalimidine.

20. A method for producing a phenolphthalein, comprising:
    reacting a phenolic compound of the formula:

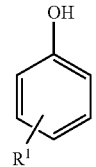

wherein $R^1$ is a hydrogen, with a phthalic anhydride compound of the formula:

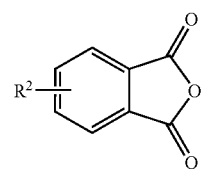

wherein $R^2$ is a hydrogen, a $C_1$-$C_{12}$ hydrocarbyl group, or a halogen, in the presence of a heterogeneous catalyst and a promoter, wherein the promoter is chlorosulphonic acid, a $C_1$-$C_{12}$ alkyl sulphonic acid, a $C_6$-$C_{12}$ aryl sulphonic acid, a $C_1$-$C_{12}$ alkyl $C_6$-$C_{12}$ aryl sulphonic acid, a halogenated $C_1$-$C_{12}$ alkyl sulphonic acid, a halogenated $C_6$-$C_{12}$ aryl sulphonic acid, a halogenated $C_1$-$C_{12}$ alkyl $C_6$-$C_{12}$ aryl sulphonic acid, trichloroacetic acid, triflic acid, boron trifluoride, or a combination comprising at least one of the foregoing promoters, to form a reaction mixture comprising a phenolphthalein compound of the formula:

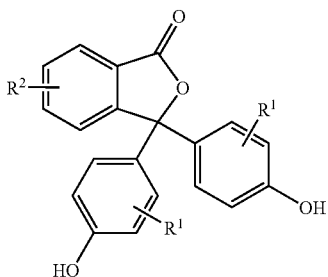

wherein each $R^1$ is a hydrogen, and $R^2$ is a hydrogen, a $C_1$-$C_{12}$ hydrocarbyl group, or a halogen; wherein the heterogeneous catalyst comprises an oxide of tungsten or an oxide of molybdenum in combination with a zirconium oxide support, a cerium oxide support, or a zirconium oxide-cerium oxide support;

quenching the reaction mixture comprising the phenolphthalein compound to provide a first quenched reaction mixture;

mixing the first quenched reaction mixture with a first organic solvent in which the phenolphthalein compound dissolves to provide a second quenched reaction mixture comprising dissolved phenolphthalein compound;

filtering the second quenched reaction mixture to provide a solid residue comprising the heterogeneous catalyst and a filtrate comprising the organic solvent and the phenolphthalein compound;

removing the organic solvent from the filtrate to provide a residue comprising the phenolphthalein compound; and regenerating the heterogeneous supported catalyst.

* * * * *